IIIIII US007298486B2

(12) United States Patent
Wang et al.

(10) Patent No.: US 7,298,486 B2
(45) Date of Patent: Nov. 20, 2007

(54) AEROSOL MOBILITY SIZE SPECTROMETER

(75) Inventors: Jian Wang, Port Jefferson, NY (US); Pramod Kulkarni, Port Jefferson Station, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 269 days.

(21) Appl. No.: 11/026,726

(22) Filed: Dec. 30, 2004

(65) Prior Publication Data

US 2006/0146327 A1    Jul. 6, 2006

(51) Int. Cl.
*G01N 21/00* (2006.01)
(52) U.S. Cl. .................. 356/438; 324/71.4; 73/28.1; 73/28.04; 356/335
(58) Field of Classification Search .............. 356/36, 356/37, 335, 437, 438; 436/148, 146, 174, 436/179; 422/100, 83, 73, 81; 73/28.01, 73/28.04, 28.1; 324/71.4
See application file for complete search history.

(56) References Cited

U.S. PATENT DOCUMENTS 6,941,005 B2 *   9/2005   Lary et al. ................. 382/133
7,029,921 B2 *   4/2006   Lee et al. .................. 436/148

OTHER PUBLICATIONS

Zhang et al.; "Resolution of the Radial Differential Mobility Analyzer for Ultrafine Particles"; *J. Aerosol Sci.* vol. 27, No. 8, pp. 1179-1200; 1996.

Tammet et al.; "Electrical Aerosol Spectrometer of Tartu University"; *Atmospheric Research*, vol. 62, pp. 315-324; 2002.
Russell et al; "Radially classified aerosol detector for aircraft-based submicron aerosol measurements"; *Journal of Atmospheric and Oceanic Technology*; 13 (3): pp. 598-609 Jun. 1996.
Zhang et al.; "Radial Differential Mobility Analyzer"; *Aerosol Science and Technology*; 23 (3): pp. 357-372 Oct. 1995.
Chen et al.; "Design and Evaluation of a Nanometer Aerosol Differential Mobility Analyzer"; *J. Aerosol Sci.*, vol. 29., No. 5, pp. 497-509, 1998.
Knutson et al. "Aerosol classification by electric mobility: apparatus, theory, and applications" *Journal of Aerosol Science*, vol. 6, Issue 6, pp. 443-451, Nov. 1975.

* cited by examiner

*Primary Examiner*—Gregory J Toatley, Jr.
*Assistant Examiner*—Abdullahi Nur
(74) *Attorney, Agent, or Firm*—Lori-Anne Neiger (57) ABSTRACT

A device for measuring aerosol size distribution within a sample containing aerosol particles. The device generally includes a spectrometer housing defining an interior chamber and a camera for recording aerosol size streams exiting the chamber. The housing includes an inlet for introducing a flow medium into the chamber in a flow direction, an aerosol injection port adjacent the inlet for introducing a charged aerosol sample into the chamber, a separation section for applying an electric field to the aerosol sample across the flow direction and an outlet opposite the inlet. In the separation section, the aerosol sample becomes entrained in the flow medium and the aerosol particles within the aerosol sample are separated by size into a plurality of aerosol flow streams under the influence of the electric field. The camera is disposed adjacent the housing outlet for optically detecting a relative position of at least one aerosol flow stream exiting the outlet and for optically detecting the number of aerosol particles within the at least one aerosol flow stream.

21 Claims, 5 Drawing Sheets

AEROSOL MOBILITY SIZE SPECTROMETER

This invention was made with Government support under contract number DE-AC02-98CH10886, awarded by the U.S. Department of Energy. The Government has certain rights in the invention.

BACKGROUND OF THE INVENTION

The present invention relates generally to devices and methods for measuring ambient aerosol distributions and properties, and more particularly, to a device and method capable of accurately measuring submicron aerosol size distributions with high time resolution and signal to noise ratio.

Aerosols refer to particles including solids, liquids and mixtures thereof suspended in a gas. Recent research has clearly demonstrated the significance of atmospheric aerosols on climate and air quality over regional and global scales. Atmospheric aerosols affect the climate by scattering and absorbing sunlight (direct effect) and by changing the microphysical structure, lifetime, and amount of clouds (indirect effect). The Intergovernmental Panel on Climate Change (IPCC) estimated that the direct and indirect effects of aerosols remain the most uncertain components in the climate system.

Prediction and mitigation of these effects require the knowledge of the spatial and temporal distributions, as well as the sources and governing processes, of the atmospheric aerosols. Among the aerosol properties needed for assessing climate impacts are size distributions and hygroscopicity. These variables determine climate forcing through their effects on light scattering and cloud formation. Particle size is also an important determinant for the study of penetration into bronchial airways and associated health effects.

Understanding and predicting the effects of aerosols on climate and air quality requires detailed characterization of ambient aerosol distributions and properties. However, due to its short lifetime, the spatial and temporal distributions of atmospheric aerosol are highly inhomogeneous. The current incomplete understanding of ambient aerosol properties, coupled with changing aerosol sources and sinks, necessitates further intensive field projects involving aircraft-based measurements. The advantages of aircraft-based measurements are obvious. These advantages include the ability to characterize 3-dimensional spatial distributions of aerosols and the ability to sample a large spatial domain within a short time. However, aircraft-base measurements are often compromised by the poor time resolution of current aerosol measurement techniques.

Conventional instruments for aerosol size distribution measurements include optical particle counter (OPC) systems and scanning mobility particle sizer (SMPS) systems, whose major component is a differential mobility analyzer (DMA). Conventional SMPS systems typically have time resolutions of about 50 seconds. The low speed of a conventional SMPS system of the prior art is a result of the system's sequential measurement method. Inside a DMA, charged aerosols migrate across flow streamlines under the influence of an electric field, and only aerosols of one size are selected and measured at one time. To obtain a complete submicron aerosol size distribution, which ranges approximately from 5 to 1000 nm, the electrical field inside the DMA has to be scanned through a wide dynamic range, and as many as 50 measurements of aerosols with different sizes are required. This takes about 50 seconds. Moreover, since only a small fraction of the aerosol is selected and measured, the counting rate of a SMPS system is very poor, which further slows down the measurements.

Even when efficiently automated, the time delay for completing a full measurement with a conventional DMA has its drawbacks. For example, a typical research aircraft travels several kilometers within a 50-second time period. Thus, accurate measurements of highly localized aerosol distributions, such as aerosols in the vicinity of a particular cloud formation or inside a pollution plume, are impossible since the aircraft will have traveled away from the localized aerosol source between the time the measurement begins to the time the measurement ends. Furthermore, due to the low sampling rate of DMA systems, measurements in clean environments are further restricted by the time required to obtain statistically significant numbers. Moreover, current SMPS systems are inadequate for detecting or measuring fast-changing size distributions of aerosol particles emitted by diesel engines and vehicles.

Other conventional aerosol measurement devices also have drawbacks. For example, conventional optical particle counters using light scattering techniques are generally only effective for measuring particle sizes greater than 200 nm. Aerosol hygroscopic property measurements, which are made using a tandem differential mobility analyzer (TDMA) system, also suffer from low time resolution and are rarely deployed in airborne studies.

Accordingly, it would be desirable to provide a measurement device which improves upon conventional DMA systems by simultaneously detecting aerosols of different sizes, thereby significantly improving measurement speed.

SUMMARY OF THE INVENTION

The present invention is a device for measuring aerosol size distribution within a sample containing aerosol particles. The device generally includes a spectrometer housing defining an interior chamber and an optical detector, such as a camera, for recording aerosol streams exiting the chamber along different flow streams. The housing includes an inlet for introducing a flow medium into the chamber in a flow direction, an aerosol injection port adjacent the inlet for introducing a charged aerosol sample into the chamber, a separation section for applying an electric field to the aerosol sample across the flow direction and an outlet opposite the inlet. In the separation section, the aerosol sample becomes entrained in the flow medium and the aerosol particles within the aerosol sample are separated by size into a plurality of aerosol flow streams under the influence of the electric field. The camera is disposed adjacent the housing outlet for optically detecting a relative position of at least one aerosol flow stream exiting the outlet and for optically detecting the number of aerosol particles within the at least one aerosol flow stream.

In a preferred embodiment, the device further includes an aerosol charger disposed adjacent the aerosol injection port of the housing and a laser source disposed adjacent the outlet. The aerosol charger imparts a predictable electrical charge distribution to the aerosol sample and the laser source illuminates the plurality of separated aerosol flow steams exiting said outlet. Also, the housing preferably has two substantially parallel walls, wherein the electric field is applied across the parallel walls and the relative position of the at least one aerosol flow stream exiting the housing outlet is optically detected relative to the parallel walls.

Additionally, the device further preferably includes a means for saturating and growing the aerosol particles through a condensation process to facilitate detecting the particles. In this regard, the housing preferably includes a growth section having a thermoelectric cooler disposed downstream of the separation section for increasing the size of saturated aerosol particles within the separated aerosol flow streams using a condensation process.

For saturating the aerosol particles, the device may include a saturator disposed adjacent the inlet of the housing for introducing a working vapor into the flow medium. The working vapor subsequently condenses on the aerosol particles within the growth section, whereby the aerosol particles increase in size. The saturator may include a reservoir for holding a working liquid, an inlet in fluid communications with the reservoir for introducing the flow medium into the reservoir, a heater adjacent the reservoir for heating the working liquid to produce the working vapor and an outlet connected to the housing inlet for introducing the working vapor and the flow medium into the interior chamber of the housing.

Alternatively, saturation may take place within a saturation section disposed between the separation section and the growth section of the housing. In this case, the saturation section of the housing may include a wick in fluid communication with the interior chamber of the housing and a heater in thermal contact with the wick. The wick is saturated with a working liquid and the heater heats the working liquid to produce the working vapor.

The housing of the present invention may be combined with other housings operating at different voltages to provide an apparatus having increased size range measurement capabilities. Specifically, the measuring apparatus of the present invention may include a first housing defining a first interior chamber and a second housing defining a second interior chamber. The first housing has a separation section for applying a first electrical field to the aerosol sample and the second housing has a separation section for applying a second electrical field to the aerosol sample. The aerosol particles within the first housing are separated by size into a plurality of aerosol flow streams having a first size range and the aerosol particles within the second housing are separated by size into a plurality of aerosol flow streams having a second size range. A camera system is disposed adjacent the outlets of the first and second housings for optically detecting a relative position of at least one aerosol flow stream from the first size range and at least one aerosol flow stream from the second size range.

Moreover, the present invention can be combined with conventional components to produce an apparatus for measuring aerosol hygroscopicity and volatility. Such an apparatus includes an aerosol charger for imparting a predictable electrical charge distribution to an aerosol sample, a differential mobility analyzer for selecting dry aerosols of a desired size, a humidifier for increasing the humidity of the dry aerosols selected by the differential mobility analyzer to produce a humidified aerosol sample, a spectrometer housing as described above for separating the aerosol particles by size into a plurality of aerosol flow streams under the influence of an electric field and a camera for optically detecting a relative position of at least one aerosol flow stream exiting the housing and for optically detecting the number of aerosol particles within the at least one aerosol flow stream. For volatility measurements, the apparatus further includes a thermal denuder connected adjacent the humidifier to be operated alternatively with the humidifier.

The present invention further involves a method for measuring aerosol size distribution within a sample containing aerosol particles. The method generally includes the step of applying an electric field across a charged aerosol sample flow, wherein the electric field separates the aerosol particles within the sample flow by size into a plurality of aerosol flow streams. The relative position of at least one aerosol flow stream is optically detected and, preferably, the number of aerosol particles within that aerosol flow stream is optically counted.

Preferably, the method of the present invention further includes the steps of illuminating the plurality of aerosol flow streams and increasing the size of the aerosol particles within the separated aerosol flow streams using a condensation process to facilitate optical detection. The condensation process preferably involves introducing a working vapor into the charged aerosol flow either before or after application of the electric field. The working vapor condenses on the aerosol particles during the condensation process to increase the size of the aerosol particles. Moreover, the electric field may be varied to produce separated aerosol flow streams of a desired range.

As a result of the present invention, a device is provided that is capable of measuring submicron aerosol size distributions and aerosol hygroscopicities within 1 second, a factor of 50 improvement in time resolution over state of the art research instruments. Thus, the device of the present invention significantly improves the ability to study the effect of atmospheric aerosol on global climate. The present invention also has significant application for studies of air pollution, combustion engine emissions, nano-material fabrication and characterization.

These and other objects, features, and advantages of this invention will become apparent from the following detailed description of illustrative embodiments thereof, which is to be read in connection with the accompanying drawings.

DETAILED DESCRIPTION OF THE PREFERRED EMBODIMENTS

Figure 1:
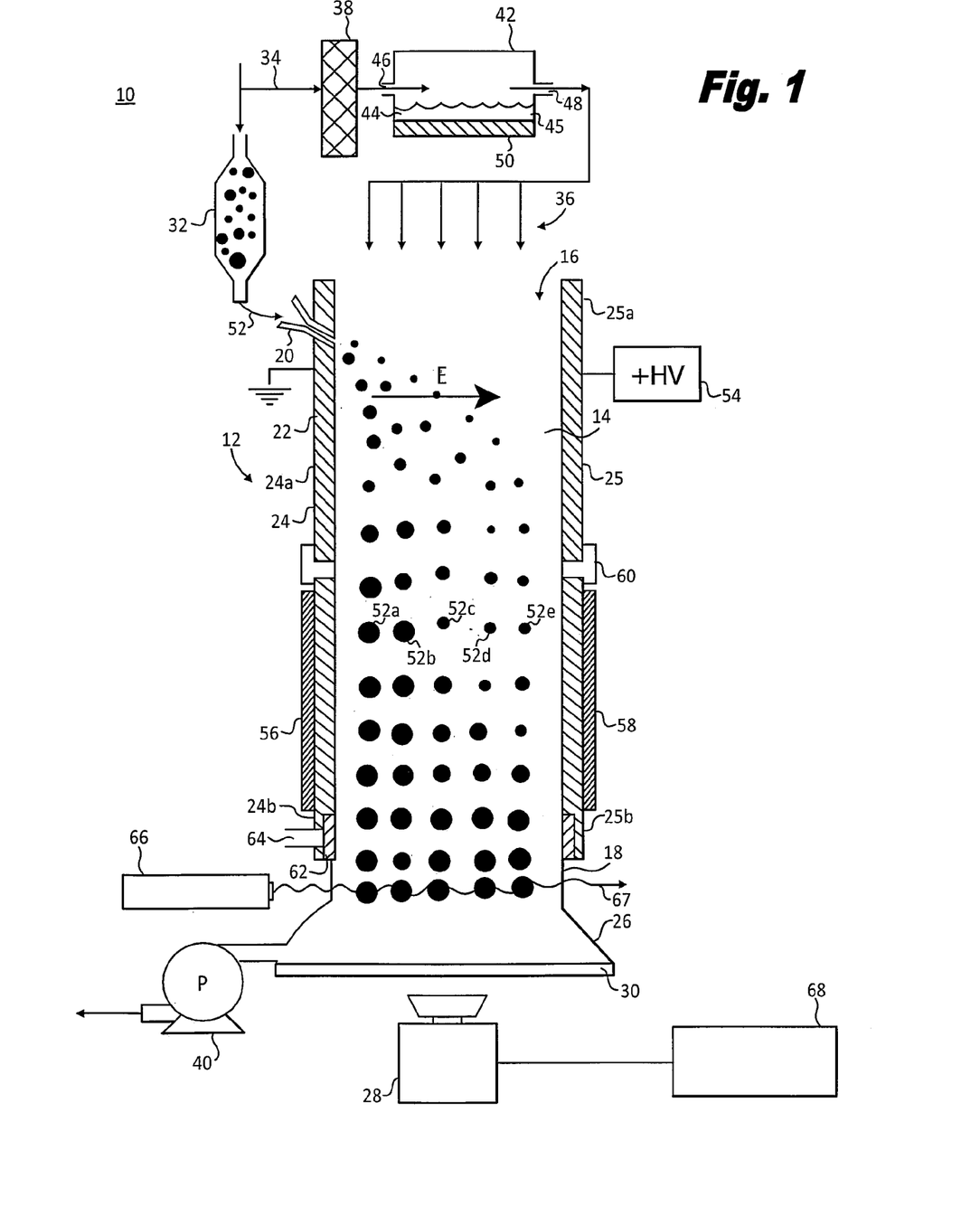
FIG. 1 is a schematic cross-sectional view of a preferred embodiment of an aerosol mobility size spectrometer formed in accordance with the present invention.

Referring first to FIG. 1, a schematic cross-section of a preferred form of an aerosol mobility size spectrometer 10, formed in accordance with the present invention, is shown. The spectrometer 10 generally includes a housing 12 and a camera 28 for detecting aerosol streams exiting the housing. The housing 12 defines an inner chamber 14 and includes an inlet 16, an outlet 18 and an aerosol injection port 20 adjacent the inlet. The inlet 16, the outlet 18 and the aerosol injection port 20 all communicate with the inner chamber 14. The housing 12 further includes a separation section 22, which applies an electric field E across the interior chamber 14, as will be described in further detail below.

The housing 12 may take various forms, but in the preferred embodiment, the housing includes two parallel walls 24 and 25 that are spaced apart a known distance. The spacing between the plates 24 and 25 is preferably about 1 cm and the widths of the plates are preferably about 10.0 cm. The plates 24 and 25 may be fixed to lateral walls (not shown) on their sides to enclose the inner chamber 14 and a hood 26 including a transparent window 30 may be attached to the outlet 18 of the housing 12. In this form, the aerosol injection port 20 takes the form of a narrow slit extending across the entire width of the plates 24 and 25 to ensure a laminar flow.

In a preferred embodiment, the spectrometer device 10 further includes an aerosol charger 32 connected to the aerosol injection port 20 of the housing 12 for imparting a predictable electrical charge distribution to an air sample being measured. In particular, a collected air sample containing aerosol particles is fed to the aerosol charger 32 where it is charged prior to being delivered to the aerosol injection port 20 of the housing 12. The aerosol sample flow rate through the aerosol charger 32 is preferably about 0.3 L/min. Suitable aerosol chargers or neutralizers are TSI Model No. 3077, which can be purchased from TSI, Inc.

Preferably, a portion 34 of the collected air sample is diverted to the inlet 16 of the housing 12 to provide a flow medium 36 within the interior chamber 14 of the housing. The diverted air portion 34 is preferably forced through a high-efficiency particulate air (HEPA) filter 38 to eliminate the aerosol particles in the air. The particle-free flow medium 36 preferably has a flow rate entering the inlet 16 of about 15.0 L/min and may be driven by a pump 40 connected to the housing hood 26 at the opposite outlet 18 of the housing. The volumetric flow rate of the flow medium 36 is preferably about 15.0 L/min and may include additional minor sheath flows through both sides of the narrow aerosol injection port slit 20 to confine the aerosol flow to the region where the flow velocity is uniform. Therefore, particles of the same size, but introduced at different locations of the injection port slit 20, experience the same electric and flow field, and travel the same distance in the direction of the electric field inside the separation section 22 discussed below.

The diverted portion 34 of the collected air sample is further preferably passed through a saturator 42 for introducing a working vapor to the flow medium 36. The saturator 42 is disposed downstream of the HEPA filter 38 and generally includes a reservoir 44, an inlet 46 and an outlet 48 in fluid communication with the reservoir and a heater 50 adjacent the reservoir. The reservoir 44 holds a working liquid 45 therein, which produces a vapor when heated by the heater 50. The working liquid 45 is preferably one that produces a very inert vapor upon heating so that the vapor will not react with the aerosol before reaching the growth section described below. Suitable working liquids include n-butanol and Fluoriner™ produced by 3M Corp. When butanol is used, the heater 50 preferably heats the butanol to about 30° C. The heater 50 may be a strip-type heater having a self-adhesive backing and electrically connected to a temperature controller to maintain temperature. Such heaters are produced by Minco Products, Inc. Thus, the inlet 46 of the saturator 42 introduces the diverted air 34 into the reservoir 44 where it becomes mixed with the working vapor produced as a result of heating the working liquid 45. The mixed working vapor and particle-free air exits the outlet 48 of the saturator 42 and becomes the flow medium 36 provided to the housing inlet 16. The flow medium 36 may further be passed through a screen (not shown) to ensure a smooth laminar flow in the housing interior chamber 14.

Upon exiting the aerosol charger 32, the charged aerosols 52 are injected through the aerosol injection port 20 into the separation section 22 of the housing 12, where it becomes entrained with the sheath flow medium 36 within the interior chamber 14. The separation section 22 of the housing 12 is preferably about 20 cm in length and includes a negative voltage source 54 for applying a constant electric field E perpendicular to the flow direction of the flow medium 36. Under the influence of this electric field E, the charged aerosols 52 are separated by size into different flow streams based on the aerosol's electrical mobility. Simply put, the smaller more mobile particles are influenced by the electric field greater than the larger particles and will, therefore, migrate further toward the charged electrode plate 25. As an example, FIG. 1 shows five flow streams 52a, 52b, 52c, 52d and 52e. However, the number of actual flow streams which can be detected is much higher.

To increase the size of the aerosol particles and, therefore, to improve detectability, particularly in the smaller ranges, the housing 12 of the present invention further preferably includes a growth section 56 disposed downstream from the separation section 22. After leaving the separation section 22, the saturated aerosol sample streams 52a, 52b, 52c, 52d and 52e enter the growth section 56 of the housing 12 where the particles in each stream are increased in size through a condensation process. The growth section 56 is essentially a condenser having a length of about 25 cm and including at least one thermoelectrical cooler 58 disposed on at least one of the parallel walls 24 and 25 of the housing 12 for cooling the aerosol sample flowing within the interior chamber 14 down to about 5° C. Suitable TEC Module thermoelectric coolers of various wattages can be obtained from Melcor, Inc.

The structure of the growth section 56 should be electrically and thermally isolated from the separation section 22 of the housing 12. To accomplish this, the parallel plates 24 and 25 may consist of plate portions 24a and 25a making up the separation section 22 and plate portions 24b and 25b making up the growth section 56 of the housing 12. All of the plate portions 24a, 24b, 25a and 25b are made from thermally and electrically conductive materials, such as stainless steel or aluminum. The plate portions 24a and 25a of the separation section 22 can be connected to the plate portions 24b and 25g of the growth section 56 by insulative couplers or flanges 60 to thermally and electrically isolate the two sections.

The growth section 56 further preferably includes at least one condensation wick 62 to absorb any excess condensation accumulating in the growth section. The condensation wick 62 may simply be a porous metal strip embedded in a recess or otherwise fixed at the bottom of the growth section wall portions 24b and 25b near the housing outlet 18 so that condensation collecting on the wall portions will be drawn downwardly toward the wick under the influence of gravity. A condensation outlet 64 is preferably in fluid communication with the wick 62 to draw condensation out of the wick. A peristaltic pump (not shown) can be used to facilitate the removal of the condensation from the wick 62 through the condensation outlet 64.

The subsequent cooling of the flow medium 36 inside the growth section 56 causes the vapor generated by the saturator 42 to condense on the aerosol particle nuclei to form droplets that are subsequently easily viewed and counted by the camera 28. The growth section 56 of the present invention generates high supersaturation that activates particles as small as 5 nm in diameter. In this manner, the aerosol particles grow into supermicron droplets.

The growth section 56 terminates at the outlet end 18 of the housing 12, where the aerosol streams 52a-e exit the housing in different relative positions due to the known electric field E applied to the flow medium 36 in the separation section 22. As mentioned above, connected at the outlet end 18 of the housing 12 is a hood 26 having a window 30. The camera 28 is positioned adjacent the outlet 18 of the housing in such a manner as to simultaneously view the aerosol streams 52a-e through the window 30 of the hood 26. The window 30 prevents deposition of grown particles onto the camera lens. Additionally, a small purge may be directed at the window so that incoming droplets will not accumulate on the window.

The major components of the camera 28 are a custom designed lens system and a frame transfer CCD. The frame transfer CCD preferably has an active area of about 12.3 mm×12.3 mm, which consists of 1024×1024 pixels, wherein each pixel is 12 μm×12 μm. The lens system preferably has a magnification ratio of 0.22 and projects a 5.6 cm×1 cm viewing area on an area of 1.23 cm×0.22 cm (1024× 182=186,368 pixels) on the CCD. It has been found that this arrangement produces a spot size of the particle image that is less than 24 μm in diameter, which is about 4 (2×2) pixels on the CCD. A suitable high-speed digital camera for use with the present invention is DALSA Model No. DS-21-01-M60.

Preferably, a laser source 66 is provided to direct a collimated sheet of light 67 perpendicular to the aerosol flow streams 52a-e exiting the outlet end 18 of the spectrometer housing 12, which illuminates the particles as they cross. The cross-section of the light sheet after collimation is preferably about 1 cm×1 mm. Any available 30-50 mWatt CW laser source providing a green laser of 532 nm wavelength can be used with the present invention. Based on the preferred geometry and flow settings, the maximum velocity of an aerosol particle is calculated to be about 38 cm/sec, whereby the grown particles will be illuminated for a minimum of 3 milliseconds as it crosses the 1 mm thick light sheet. The thus illuminated supermicron aerosol droplets are then easily detected by the camera 28 and can be counted by a data acquisition system 68 connected to the camera 28.

Figure 2:
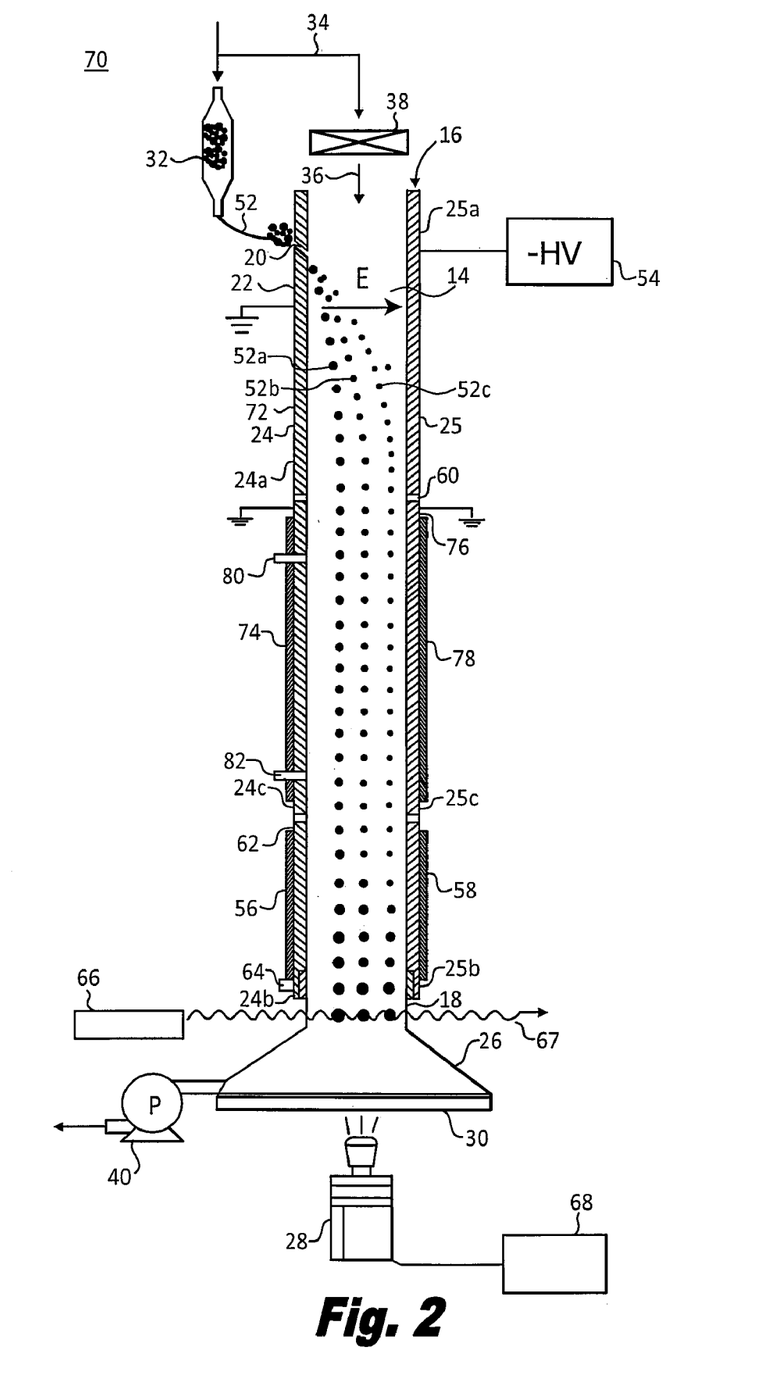
FIG. 2 is a schematic cross-sectional view of an alternative embodiment of an aerosol mobility size spectrometer of the present invention.

An alternative embodiment of the present invention is shown in FIG. 2, wherein like parts have the same reference numerals. In the alternative device 70, shown in FIG. 2, the saturation function for introducing a working vapor to the flow medium 36 has been incorporated within the spectrometer housing. In particular, the housing 72 of this device 70 includes a saturation section 74 disposed between the separation section 22 and the growth section 56. The saturation section 74 is preferably about 45 cm in length and includes thermally conductive parallel plate portions 24c and 25c, which, together with the plate portions 24a and 25a of the separation section and the plate portions 24b and 25b of the growth section, define the interior chamber 14 of the housing 12.

Again, it is important to electrically and thermally isolate the saturation section 74 from both the separation section 22 and the growth section 56. This is again accomplished by connecting respective wall portions with insulative couplings 60. Also, the wall portions 24c and 25c of the saturation section are preferably electrically grounded.

The saturation section 74 of this embodiment includes at least one wick 76 disposed on the inner surface of at least one of the parallel wall portions 24c and 25c and at least one heating tape 78 disposed adjacent the wick, for example, on the outer surface of the parallel wall. The wick 76 is soaked with an organic liquid such as n-butanol, which becomes vaporized upon heating by the heating tape 78 to a temperature of about 30° C. Here too, the wick 76 may be made from a porous or semi-porous metal sheet having pores to absorb the working fluid. The wick may be embedded in a recess or otherwise fixed on the inner surface of the wall portions 24c and 25c facing the interior chamber 14 of the housing 12. A saturation liquid injection port 80 in fluid communication with the wick 76 may be provided for injecting the working liquid into the wick. Similarly, a saturation liquid evacuation port 82 in fluid communication with the wick 76 may be provided for withdrawing excess working liquid from the wick.

Like the saturator 42 described above, the saturation section 74 of the housing works to introduce a working vapor into the flow medium 36, which subsequently condenses on the aerosol particles in the growth section 56 to increase the size of the particles for easy detection. However in this case, the flow medium 36 is saturated with the organic vapor after separation into size-dependent aerosol streams 52a, 52b and 52c, as shown in FIG. 2.

Figure 3:
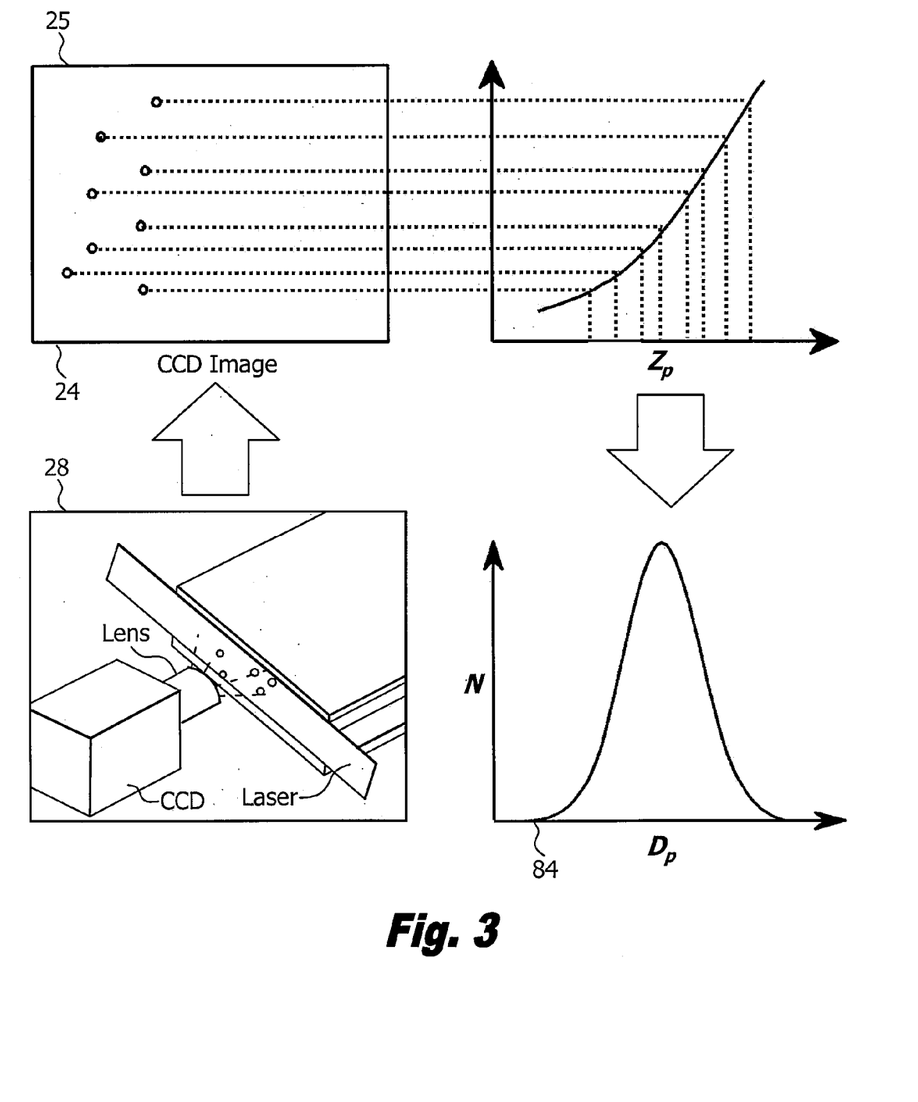
FIG. 3 is a graphical representation of a typical aerosol measurement taken by the aerosol mobility size spectrometer of the present invention.

In both embodiments, the imaging system 28 and 68 records size-dependent particle positions and their numbers, which are then used to derive particle size distribution spectrum, as shown in FIG. 3. Specifically, the camera 28 records a CCD image of all of the particle streams 52a-52e exiting the outlet 18 of the spectrometer housing 12. The relative position of each stream 52a-52e between the parallel walls 24 and 25 of the housing 12 can be determined and the number of aerosol particles at each position can be counted based on image pixel distribution using suitable data acquisition software. The digital camera 28 is preferably operated at a readout speed of 10 fps so that the probability that two particles are detected at the same location during the 0.1 second exposure time is very small. Also, at a readout speed of 10 fps, the signal to noise ratio for grown particles of 20 microns in diameter is about 200. Therefore, grown particles can be reliably detected using the imaging system of the present invention.

Thus, the aerosol mobility size spectrometer of the present invention addresses the need to improve measurement speed through a new approach. Specifically, particles of different sizes are simultaneously measured, wherein the size of the particles and the number of particles of each size can be determined. By eliminating the necessity to scan through the wide range of particles sizes, complete size distributions can be obtained in 1 second or less. Additionally, since all charged particles are measured simultaneously, the AMSS of the present invention has a much better counting rate than conventional DMA systems.

The aerosol mobility size spectrometer (AMSS) of the present invention is able to simultaneously measure aerosols spanning one-decade in electrical mobility range (i.e. the maximum mobility of particle is 10 times the minimum mobility of particles measured by the AMSS). However, the electric field E applied across the separation section 14 can vary depending on the aerosol measurement range desired. For example, it has been found that an electric field E of about −116 V is preferred for a spectrometer device measuring aerosols in the range of about 15-47 nm, an electric field E of about −1,157 V is preferred for a spectrometer measuring aerosols in the range of about 46-176 nm and an electric field E of about −11,570 V is preferred for a spectrometer measuring aerosols in the range of about 173-1,000 nm. Thus, the device can be utilized in a sequential fashion in which an aerosol sample can be injected into a single device and subjected to a first electric field $E_1$ for a first predetermined period of time and then subjected to a second electric field $E_2$, for a second predetermined period of time and so on.

Figure 4:
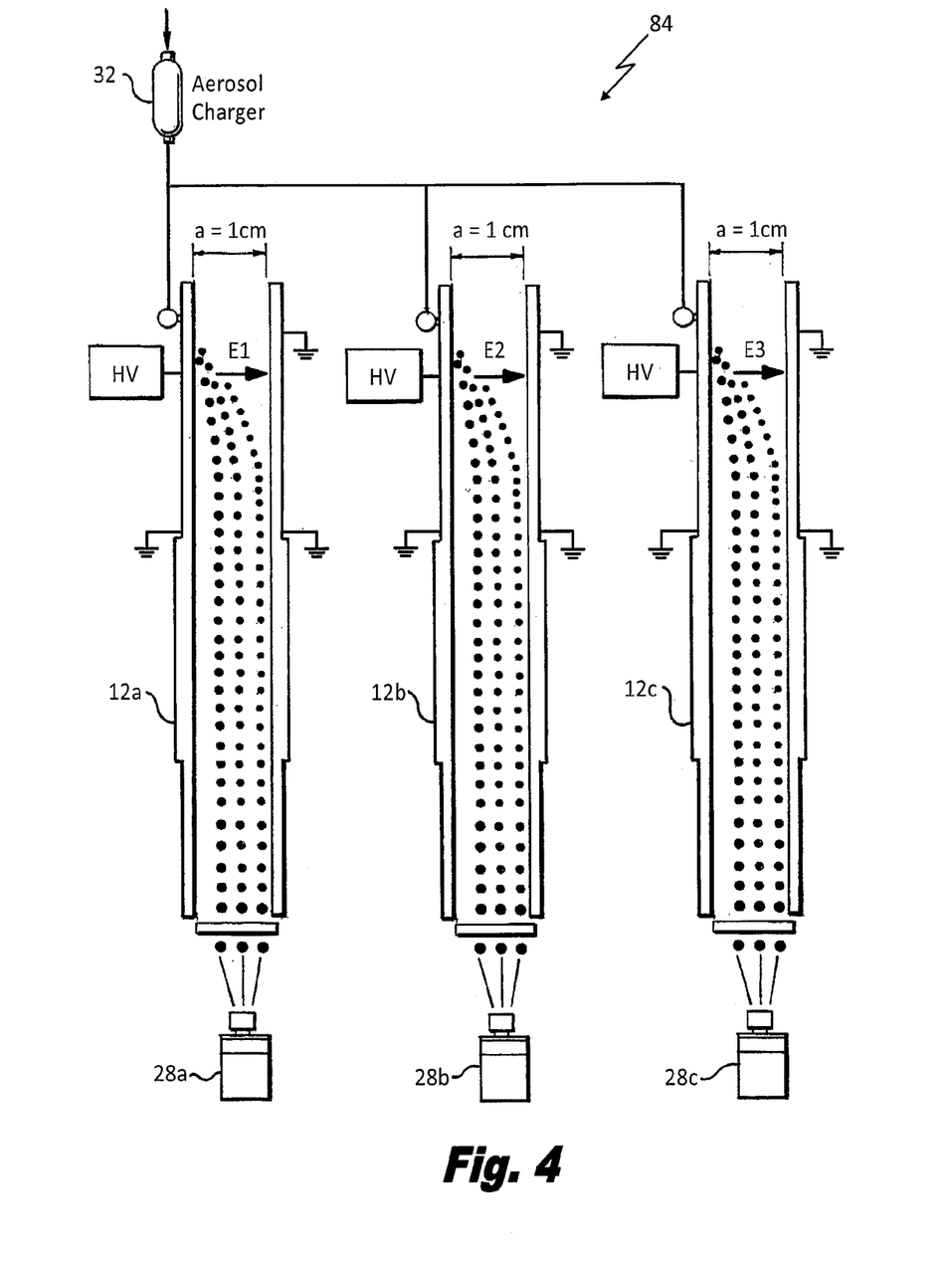
FIG. 4 is a block diagram of an apparatus for measuring aerosol size distribution using three aerosol mobility size spectrometers of the present invention.

However, to eliminate the time required for successive testing, in a preferred embodiment shown in FIG. 4, the device of the present invention can be utilized as part of a system or apparatus 84 having three or more housings 12a, 12b and 12c operating simultaneously at different respective voltages E1, E2 and E3. In particular, to cover the complete size range of aerosols, a first housing 12a operating at a first voltage E1 of −115V measures aerosols with a first size range of about 15-48 nm. The first housing is preferably operated in parallel with a second housing 12b operating at a second voltage E2 of −1,157V and measuring aerosols with a second size range of about 48-180 nm. Finally, a third housing 12c is operated in parallel with the first and second housings 12a and 12b and applies a third voltage E3 of −11,570V and measures aerosols having a third size range of about 180-1000 nm. A single camera system or three cameras 28a, 28b and 28c can be utilized to record the aerosol flow streams exiting their respective housings. Aerosol sizes greater than 1000 nm can be measured by a conventional optical particle counter, which may be operated in parallel with the three AMSS housing system of the present invention.

Figure 5:
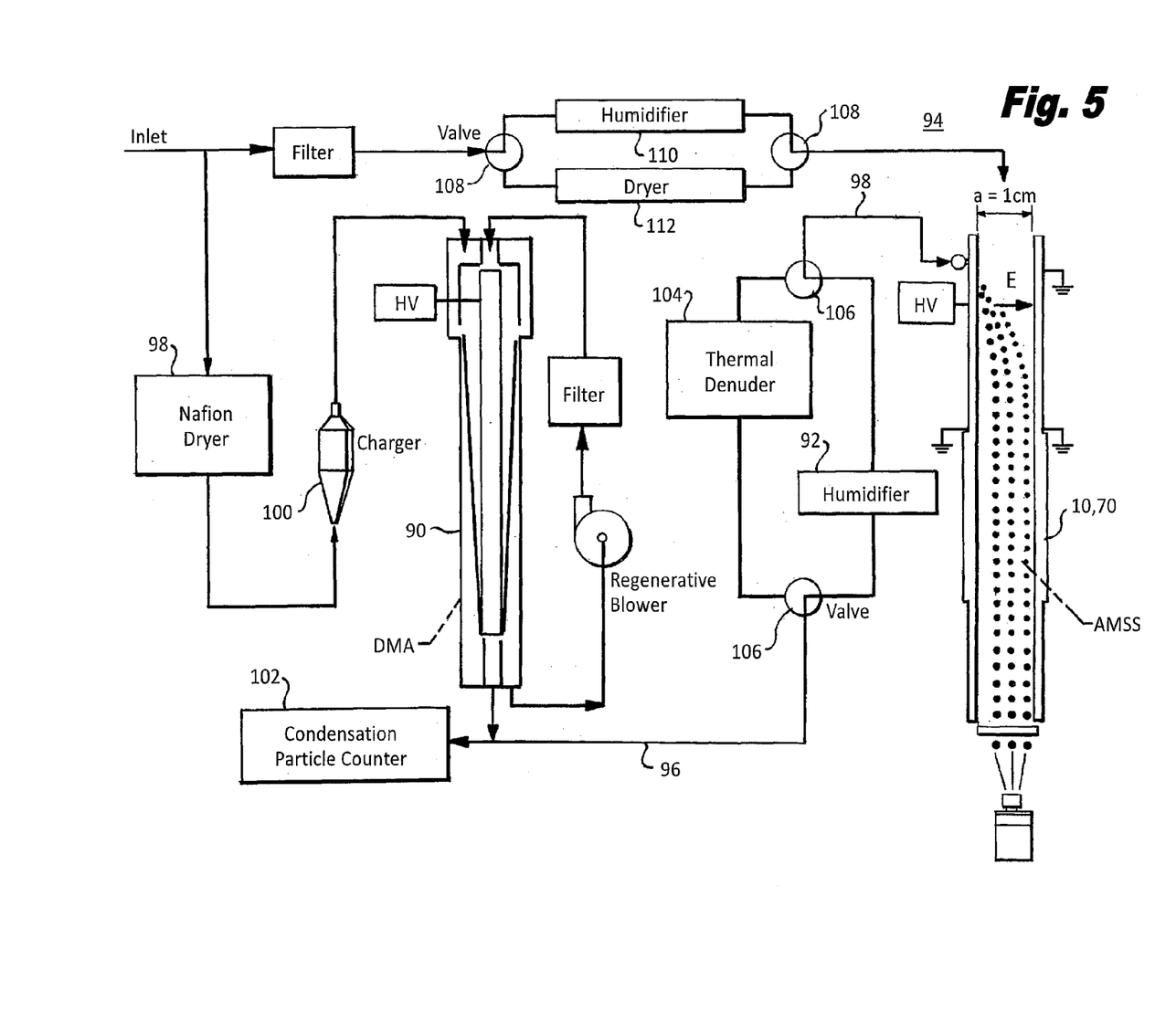
FIG. 5 is a block diagram of an aerosol hygroscopicity/volatility spectrometer (AHVS) formed in accordance with the present invention.

Moreover, as schematically shown in FIG. 5, the present invention 10, 70 may also be combined with a conventional differential mobility analyzer (DMA) 90 and a humidifier 92 to form an aerosol hygroscopicity/volatility spectrometer (AHVS) 94, which measures growth of dry aerosols when they are exposed to high relative humidity and further measures the particles' volatility. Generally, the differential mobility analyzer (DMA) 90 selects dry aerosols 96 of a desired size in a known manner. These classified aerosols 96 are delivered to a conventional humidifier 92 where they are subsequently humidified to a high relative humidity (e.g. 85%). Although starting at the same size, the aerosols 96 of different chemical composition will grow to different final sizes when subjected to a high relative humidity. The resulting humidified aerosols 98 of varying sizes can be introduced to the AMSS 10, 70 of the present invention where the resulting size distribution of these aerosols after humidification can then measured.

More specifically, an aerosol sample is first dried in a nafion dryer 98 and then introduced into an aerosol charger 100, where the aerosol reaches a steady state charging distribution. A conventional DMA 90 can be used to select a dry monodisperse aerosol at a specified size. The monodispersed aerosol is then split into two flows. One of the two flows is sent to a condensation particle counter (CPC) 102 that monitors the concentration of the monodispersed aerosol. The other flow is directed to a conventional humidifier 92 where the dry monodisperse aerosol is humidified to 85% relative humidity (RH). Connected downstream of the humidifier is the aerosol mobility size spectrometer (AMSS) 10, 70 of the present invention which measures the size distribution of the humidified aerosol. The aerosol hygroscopicity is derived from the size of the mondispersed dry aerosol and its size distribution after humidification.

The apparatus 94 shown in FIG. 5 can also be adapted for aerosol volatility measurements (AHVS). In this case, a thermal denuder 104 is connected adjacent the humidifier 92 to be operated alternatively with the humidifier. Monodispersed aerosol is heated inside the thermal denuder 104 to evaporate nonrefractory species. The size distribution of remaining refractory species is then measured downstream by the AMSS 10, 70. Computer-controlled valves 106 will direct aerosol to the humidifier 92 and the thermal denuder 104 alternately, and another set of valves 108 will switch sheath flow for the AMSS 10, 70 between a humidifier 110 and a dryer 112 accordingly.

The thermal denuder 104 is preferably operated at about 300° C. to evaporate nonrefractory species such as sulfate, nitrate, and organics. Species surviving the thermal denuder will be mainly EC, sea salt, and mineral dust. Different refractory species can be inferred from their sizes and measurement conditions. For example, refractory species in fine particles is mostly elemental carbon while refractory species found in coarse particles are more likely to be sea salt or mineral dust depending on location. Since the size distribution of atmospheric aerosol is much broader than the DMA transfer function, the size distribution of monodispersed aerosol can be derived from the DMA transfer function and concentration measured by the CPC 102. By comparing size distributions of selected aerosol before and after the thermal denuder, aerosol volatility and concentrations of refractory species are obtained.

Similarly, hygroscopicity measurements can also be used to infer aerosol chemical composition as various major aerosol species have different water uptake at 85% RH. By combining the hygroscopicity and volatility measurements, concentrations of major aerosol species can be derived. These include sulfate (hydrophilic and volatile), organics (largely hydrophobic and volatile), sea salt (hydrophilic and refractory), elemental carbon, and mineral dust (both hydrophobic and refractory, but likely to appear in different particles sizes).

Aerosol hygroscopicity and volatility measurements will also provide aerosol-mixing state, which is important for determining aerosol absorption. A bimodal (or multimodal) distribution after the monodispersed aerosol is humidified or heated indicates the aerosol is externally mixed, while a unimodal distribution is often associated with internally mixed aerosols. Combined with current composition measurements onboard a research aircraft, the chemical composition mixing state inferred from AHVS measurements will provide a more complete picture of the aerosol composition, which is critical to understand radiative effects of atmospheric aerosols.

For most atmospheric aerosol, the growth factor at 85% RH ranges from 0.8 to 2.2. (The growth factor is the ratio of particle diameter at 85% RH to the diameter of dry particles). As discussed above, the measurement range of a single AMSS unit is 1 decade in electrical mobility, which is sufficient to cover the entire size spectrum of the humidified aerosol. To obtain size-resolved aerosol hygroscopicity, the voltage of the classifying DMA is ramped exponentially (similar to SMPS measurements) to select monodispersed aerosol of different sizes. At the same time, the voltage applied to the AMSS 10, 70 will be ramped accordingly so that the measurement range of the AMSS covers the entire size spectrum of the humidified aerosol. The same method will be used for volatility measurements.

By utilizing the AMSS 10, 70 of the present invention downstream of a conventional DMA 90, the AHVS 94 substantially increases the speed of hygroscopicity and volatility measurements. Moreover, since atmospheric aerosols have growth factors ranging from about 0.8 to 2.2 (at 85% relative humidity, a single AMSS 10, 70 of the present invention will generally cover the size range of humidified aerosols.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

The invention claimed is:

1. A device for measuring aerosol size distribution within a sample containing aerosol particles, the device comprising:
    a chamber including an inlet for introducing a flow medium therein in a flow direction, an aerosol injection port adjacent said inlet for introducing a charged aerosol sample into said chamber wherein the aerosol sample becomes entrained in said flow medium, a separation section for applying an electric field to the aerosol sample across said flow direction wherein the aerosol particles within the aerosol sample are separated by size into a plurality of aerosol flow streams under the influence of said electric field, and an outlet opposite said inlet for transporting said plurality of separated aerosol flow streams out of said chamber; and
    an optical detector disposed adjacent said chamber outlet for optically detecting a relative position of at least one aerosol flow stream exiting said outlet.

2. A device as defined in claim 1, further comprising an aerosol charger disposed adjacent said aerosol injection port of said chamber for imparting a predictable electrical charge distribution to said aerosol sample.

3. A device as defined in claim 1, further comprising a laser source disposed adjacent said outlet of said chamber for illuminating said plurality of separated aerosol flow steams exiting said outlet.

4. A device as defined in claim 1, wherein said chamber is defined by a housing having two substantially parallel walls, said electric field being applied across said parallel walls and said relative position of said at least one aerosol flow stream exiting said housing outlet being optically detected relative to said parallel walls.

5. A device as defined in claim 1, wherein said chamber further includes a growth section disposed downstream of said separation section for increasing the size of the aerosol particles within said separated aerosol flow streams using a condensation process.

6. A device as defined in claim 4, wherein said growth section of said chamber comprises a thermoelectric cooler for driving said condensation process.

7. A device as defined in claim 5, further comprising a saturator disposed adjacent said inlet of said chamber for introducing a working vapor into said flow medium, said working vapor condensing on the aerosol particles within said growth section, whereby the aerosol particles increase in size.

8. A device as defined in claim 7, wherein said saturator comprises a reservoir for holding a working liquid, an inlet in fluid communications with said reservoir for introducing said flow medium into said reservoir, a heater adjacent said reservoir for heating said working liquid to produce said working vapor and an outlet connected to said chamber inlet for introducing said working vapor and said flow medium into said chamber.

9. A device as defined in claim 5, wherein said chamber further includes a saturation section disposed between said separation section and said growth section for introducing a working vapor into said separated aerosol flow streams, said working vapor condensing on the aerosol particles within said growth section whereby the aerosol particles increase in size.

10. A device as defined in claim 9, wherein said saturation section of said chamber comprises a wick and a heater in thermal contact with said wick, said wick being saturated with a working liquid and said heater heating said working liquid to produce said working vapor.

11. A method for measuring aerosol size distribution within a sample containing aerosol particles, the method comprising the steps of:
    applying an electric field across a flow of charged aerosol particles, said electric field separating said charged aerosol particles to form a plurality of aerosol flow streams, each of said aerosol flow streams containing particles of substantially the same size; and
    optically detecting a relative position of at least one said flow stream of charged aerosol particles.

12. A method as defined in claim 11 further comprising the step of optically detecting the number of aerosol particles within said at least one aerosol flow stream.

13. A method as defined in claim 11, further comprising the step of illuminating said plurality of aerosol flow streams to facilitate optical detection.

14. A method as defined in claim 11, further comprising the step of increasing the size of the aerosol particles within said separated aerosol flow streams using a condensation process to facilitate optical detection.

15. A method as defined in claim 14, further comprising the step of introducing a working vapor into said charged aerosol flow before application of said electric field, said working vapor condensing on said aerosol particles during said condensation process to increase the size of the aerosol particles.

16. A method as defined in claim 14, further comprising the step of introducing a working vapor into said separated aerosol flow streams after application of said electric field, said working vapor condensing on said aerosol particles during said condensation process to increase the size of the aerosol particles.

17. A method as defined in claim 11, wherein said electric field is applied across two substantially parallel walls on opposite sides of said aerosol sample flow and said relative position of said at least one aerosol flow stream is optically detected relative to said parallel walls.

18. A method as defined in claim 11, further comprising the step of varying said electrical field to produce separated aerosol flow streams of a desired range.

19. An apparatus for measuring aerosol size distribution within a sample containing aerosol particles, the device comprising:
    a first housing defining a first interior chamber, said first housing including an inlet for introducing a flow medium into said first chamber in a flow direction, an aerosol injection port adjacent said inlet for introducing a charged aerosol sample into said first chamber wherein the aerosol sample becomes entrained in said flow medium, a separation section for applying a first electrical field to the aerosol sample across said flow direction wherein the aerosol particles within the aerosol sample are separated by size into a plurality of aerosol flow streams having a first size range under the influence of said first electric field, and an outlet opposite said inlet for transporting said plurality of separated aerosol flow steams having said first size range out of said first interior chamber;

a second housing defining a second interior chamber, said housing including an inlet for introducing a flow medium into said second chamber in a flow direction, an aerosol injection port adjacent said inlet for introducing a charged aerosol sample into said second chamber wherein the aerosol sample becomes entrained in said flow medium, a separation section for applying a second electrical field to the aerosol sample across said flow direction wherein the aerosol particles within the aerosol sample are separated by size into a plurality of aerosol flow streams having a second size range under the influence of said second electric field, and an outlet opposite said inlet for transporting said plurality of separated aerosol flow steams having said second size range out of said second interior chamber; and a camera system disposed adjacent said first and second housing outlets for optically detecting a relative position of at least one aerosol flow stream from said first size range and at least one aerosol flow stream from said second size range.

20. An apparatus for measuring the growth of dry aerosols exposed to high relative humidity comprising:

an aerosol charger for imparting a predictable electrical charge distribution to an aerosol sample;

a differential mobility analyzer for selecting dry aerosols of a desired size from said charged aerosol sample;

a humidifier for increasing the humidity of the dry aerosols selected by said differential mobility analyzer;

a housing defining an interior chamber, said housing including an inlet for introducing a flow medium into said chamber in a flow direction, an aerosol injection port adjacent said inlet for introducing the charged aerosols into said chamber, a separation section for applying an electric field to the charged aerosols across said flow direction wherein the charged aerosols are separated by size into a plurality of aerosol flow streams under the influence of said electric field, and an outlet opposite said inlet for transporting said plurality of separated aerosol flow streams out of said interior chamber; and a camera disposed adjacent said housing outlet for optically detecting a relative position of at least one aerosol flow stream exiting said outlet and for optically detecting the number of aerosol particles within said at least one aerosol flow stream.

21. An apparatus as defined in claim 20, further comprising a thermal denuder for adapting the apparatus for aerosol volatility measurements.

* * * * *